United States Patent
Shi et al.

(10) Patent No.: US 12,398,089 B2
(45) Date of Patent: Aug. 26, 2025

(54) METHOD FOR PREPARING ORGANIC CARBOXYLIC ESTER BY USING COMBINED CATALYST OF ARYL BIDENTATE PHOSPHINE LIGAND

(71) Applicants: NANJING CHENGZHI CLEAN ENERGY CO. LTD., Nanjing (CN); LANZHOU INSTITUTE OF CHEMICAL PHYSICS, CAS, Lanzhou (CN)

(72) Inventors: Feng Shi, Lanzhou (CN); Weibing Tang, Lanzhou (CN); Hongli Wang, Lanzhou (CN); Jing Zhao, Lanzhou (CN); Kang Zhao, Lanzhou (CN); Jian Wang, Lanzhou (CN); Dongcheng Wei, Lanzhou (CN); Xiao Li, Lanzhou (CN)

(73) Assignees: NANJING CHENGZHI CLEAN ENERGY CO. LTD., Nanjing (CN); LANZHOU INSTITUTE OF CHEMICAL PHYSICS, CAS, Lanzhou (CN)

( * ) Notice: Subject to any disclaimer, the term of this patent is extended or adjusted under 35 U.S.C. 154(b) by 858 days.

(21) Appl. No.: 17/753,174

(22) PCT Filed: Oct. 30, 2020

(86) PCT No.: PCT/CN2020/125030
§ 371 (c)(1),
(2) Date: Feb. 22, 2022

(87) PCT Pub. No.: WO2021/129138
PCT Pub. Date: Jul. 1, 2021

(65) Prior Publication Data
US 2022/0298097 A1   Sep. 22, 2022

(30) Foreign Application Priority Data
Dec. 27, 2019   (CN) .......................... 201911377577.3

(51) Int. Cl.
*C07C 67/38* (2006.01)
*B01J 31/24* (2006.01)

(52) U.S. Cl.
CPC ........... *C07C 67/38* (2013.01); *B01J 31/2409* (2013.01); *B01J 2231/321* (2013.01); *B01J 2531/0213* (2013.01); *B01J 2531/824* (2013.01); *C07C 2531/24* (2013.01)

(58) Field of Classification Search
CPC .. C07C 67/38; C07C 2531/24; B01J 31/2409; B01J 2231/321; B01J 2531/0213; B01J 2531/824
See application file for complete search history.

(56) References Cited

U.S. PATENT DOCUMENTS

| | | | |
|---|---|---|---|
| 6,284,919 B1 | 9/2001 | Pearson et al. | |
| 6,476,255 B1 | 11/2002 | Hadden et al. | |
| 2001/0051745 A1 | 12/2001 | Pearson et al. | |
| 2005/0085671 A1 | 4/2005 | Bohnen et al. | |
| 2017/0022137 A1* | 1/2017 | Dong ...................... | B01J 31/24 |
| 2017/0022234 A1 | 1/2017 | Jennerjahn et al. | |
| 2017/0174610 A1* | 6/2017 | Haoquan ................ | C07C 67/38 |

FOREIGN PATENT DOCUMENTS

| | | |
|---|---|---|
| CN | 1063277 A | 8/1992 |
| CN | 1276779 A | 12/2000 |
| CN | 101001827 A | 7/2007 |
| CN | 101003456 A | 7/2007 |
| CN | 101844981 A | 9/2010 |
| CN | 101977887 A | 2/2011 |
| CN | 102531890 A * | 7/2012 |
| CN | 103319337 A | 9/2013 |
| CN | 106366126 A | 2/2017 |
| CN | 107628948 A | 1/2018 |
| CN | 111087306 A | 5/2020 |
| EP | 0495547 A2 | 7/1992 |
| EP | 0499329 A1 | 8/1992 |
| WO | 1996019434 A1 | 6/1996 |
| WO | 2004014552 A1 | 2/2004 |
| WO | 2013107904 A1 | 7/2013 |

OTHER PUBLICATIONS

Dorwald, F.Z., Side reactions in Organic Synthesis, Wiley: VCH, Weinheim pp. IX of Preface and pp. 1-15, (Year: 2005).*
Khokarale, S.G., et al., Zwitterion enhanced performance in palladium-phosphine catalyzed ethylene methoxycarbonylation, Catalysis Communications, vol. 44, Jan. 10, 2014, pp. 73-75.
Amézquita-Valencia, M., et al., Regioselective Alkoxycarbonylation of Allyl Phenyl Ethers Catalyzed by Pd/dppb Under Syngas Conditions, J. Org. Chem. 2016, 81, 3860-3867.
Ferreira, et al., Borate Esters as Alternative Acid Promoters in the Palladium-Catalyzed Methoxycarbonylation of Ethylene, Angew. Chem. Int. Ed. 2007, 46, 2273-2275.
Robertson, R.A.M., et al., Unusual products from CO/ethene reactions catalysed by b-ketophosphine and related complexes of rhodium, Chem. Commun., 2001, 47-48.
Pugh, R.I., et al., Tandem isomerisation-carbonylation catalysis: highly active palladium(II) catalysts for the selective methoxycarbonylation of internal alkenes to linear esters, Chem. Commun., 2001, 1476-1477.
Dong, K., et al., Cooperative catalytic methoxycarbonylation of alkenes: uncovering the role of palladium complexes with hemilabile ligands, Chem. Sci., 2018, 9, 2510.
Li, H., et al., The scope and mechanism of palladium-catalysed Markovnikov alkoxycarbonylation of alkenes, Nature Chemistry vol. 8, pp. 1159-1166 (2016).

(Continued)

*Primary Examiner* — Yate' K Cutliff
(74) *Attorney, Agent, or Firm* — AVEK IP, LLC

(57) ABSTRACT

Disclosed is a method for preparing an organic carboxylic ester by using a combined catalyst of an aryl bidentate phosphine ligand. The method includes subjecting a terminal olefin, carbon monoxide, and an alcohol to a hydroesterification reaction in the presence of a combined catalyst of a palladium compound, an aryl bidentate phosphine ligand, and an acidic additive, to generate an organic carboxylic ester having one more carbon atom than the terminal olefin.

16 Claims, No Drawings

(56) References Cited

OTHER PUBLICATIONS

Dong, K., et al., Highly active and efficient catalysts for alkoxycarbonylation of alkenes, Nature Communications vol. 8, Article No. 14117 (2017).
Dong, K., et al., Efficient Palladium-Catalyzed Alkoxycarbonylation of Bulk Industrial Olefins Using Ferrocenyl Phosphine Ligands, Angew. Chem. Int. Ed. 2017, 56, 5267-5271.

* cited by examiner

METHOD FOR PREPARING ORGANIC CARBOXYLIC ESTER BY USING COMBINED CATALYST OF ARYL BIDENTATE PHOSPHINE LIGAND

CROSS REFERENCE TO RELATED APPLICATIONS

This application is the United State national stage entry under 37 U.S.C. 371 of PCT/CN2020/125030, filed on Oct. 30, 2020, which claims priority to Chinese application number 201911377577.3, filed on Dec. 27, 2019, the disclosure of which are incorporated by reference herein in their entireties.

FIELD OF THE DISCLOSURE

The present disclosure relates to a method for preparing an organic carboxylic ester, in particular to a method for preparing an organic carboxylic ester by a combined catalyst of an aryl bidentate phosphine ligand. The disclosure belongs to the technical field of chemical synthesis.

BACKGROUND

Organic carboxylic esters are an important class of oxygen-containing compounds, which are widely used in the fields of fine chemical products, medicines, pesticides, food additives, fragrances, coatings, and paints. For example, methyl propionate is widely used in the food, feed, and cosmetic industries as a solvent, additive, preservative, or fragrance. In addition, it is also an important chemical intermediate, and a key raw material for the production of polymethyl methacrylate (PMMA). PMMA has the advantages of good weather resistance, moderate density, rigidity, stability, and transparency, and thus is widely used in automotive, LED core element materials, construction, aviation, and other fields. Therefore, it is of great significance to develop an efficient synthesis method of organic carboxylic esters.

The hydroesterification of olefins is a reaction of a terminal olefin with carbon monoxide and an alcohol in the presence of a metal compound/a phosphine ligand to generate an ester having one more carbon atom than the terminal olefin. It is the most atomically economical and simple method among many methods for synthesizing organic carboxylic esters. A general equation for the hydroesterification of olefins is as follows:

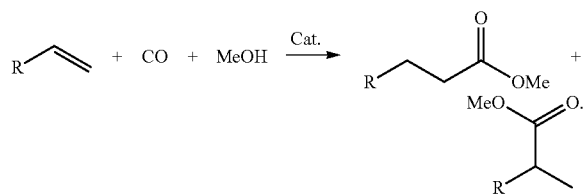

At present, the reported catalyst systems consist essentially of a central metal, a related phosphine ligand, and an acid additive. The central metal is a transition metal of VIII and IB groups, such as Rh, Pd, Ni, Co, Cu. Among them, the metal Pd is the most studied. The related phosphine ligand such as alkyl phosphine, cycloalkyl phosphine, bidentate phosphine has been described in many patent references, such as EP-A-04489472, EP-A-0499329, EP-A-0495547, US2005085671A1, U.S. Pat. No. 6,284,919B1, US2001051745A1, and U.S. Pat. No. 6,476,255B1. In particular, Lucite company disclosed a group of bidentate phosphines with a substituted aryl bridge, i.e. 1,2-bis(di-tert-butylphosphinomethyl) benzene (DTBPMB), which allowed for a significantly higher reaction rate than those previously disclosed catalysts and little or no impurities produced, and meanwhile a high conversion rate (Chem. Commun. 1999, 1877-1878; WO 96/19434; WO 2004/014552 A1). In addition, Evonik Degussa also disclosed 1,1'-bis(tert-butylphenylphosphino)-ferrocene ligand, which exhibited high catalytic performance for the hydroesterification of olefins (Angew. Chem. Int. Ed., 2017, 56 (19), 5267-5271; US 2017/0022234 A1). These two ligands are currently the most efficient ligands in olefin hydroesterifications. These examples pointed out that the important factors that affect high activity derive from the structure of the tertiary carbon alkyl phosphine ligand. Although these two ligands show good performance in the hydroesterification, the alkyl phosphine ligand is extremely unstable in the air, which would inevitably increase the investment cost for industrial applications. Therefore, there is an urgent need to develop a ligand for olefin hydroesterification with good stability, simple synthesis method and excellent catalytic performance.

SUMMARY

The following presents a simplified summary of the invention to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

An object of the present disclosure is to provide a method for preparing an organic carboxylic ester by an olefin hydroesterification catalyzed by a combined catalyst of an aryl bidentate phosphine ligand. The method according to the present disclosure includes subjecting a terminal olefin, carbon monoxide, and an alcohol to a hydroesterification reaction in an organic solvent in the presence of a combined catalyst of a palladium compound, an aryl bidentate phosphine ligand, and an acidic additive, to generate an organic carboxylic ester having one more carbon atom than the terminal olefin.

In some embodiments, in the combined catalyst of a palladium compound, an aryl bidentate phosphine ligand, and an acidic additive, a molar ratio of the aryl bidentate phosphine ligand to the palladium compound ranges from 0.1:1 to 100:1, and a molar ratio of the acidic additive to the palladium compound ranges from 0.1:1 to 100:1.

In some embodiments, in the combined catalyst of a palladium compound, an aryl bidentate phosphine ligand, and an acidic additive, the molar ratio of the aryl bidentate phosphine ligand to the palladium compound ranges from 2:1 to 10:1, and the molar ratio of the acidic additive to the palladium compound ranges from 2:1 to 20:1.

In some embodiments, in the combined catalyst of a palladium compound, an aryl bidentate phosphine ligand, and an acidic additive, the aryl bidentate phosphine ligand has a structural formula of

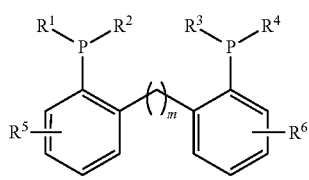

Here, m is 1 or 2.

Each of $R^1$, $R^2$, $R^3$ and $R^4$ is independently selected from the group consisting of $C_{6-20}$ aryl, $C_{3-20}$ heteroaryl, substituted $C_6$-$C_{20}$ aryl, and substituted $C_3$-$C_{20}$ heteroaryl.

Each of $R^5$ and $R^6$ is independently selected from the group consisting of hydrogen, $C_{1-18}$ alkyl, methoxy, phenyl, phenoxy, halogen, trifluoromethyl, cyano, and nitro.

In some embodiments, in the substituted $C_{6-20}$ aryl and substituted $C_{3-20}$ heteroaryl, a substituent is selected from the group consisting of —$C_{1-12}$ alkyl, —$C_{3-12}$ cycloalkyl, —$C_{3-12}$ heterocycloalkyl, —$C_{6-20}$ aryl, —$C_{3-20}$ heteroaryl, —O—$C_{1-12}$ alkyl, —O—$C_{1-12}$ alkyl-$C_{6-20}$ aryl, —O—$C_{3-12}$ cycloalkyl, —S—$C_{1-12}$ alkyl, —S—$C_{3-12}$ cycloalkyl, —COO—$C_{1-12}$ alkyl, —COO—$C_{3-12}$ cycloalkyl, —CONH—$C_{1-12}$ alkyl, —CONH—$C_{3-12}$ cycloalkyl, —CO—$C_{1-12}$ alkyl, —CO—$C_{3-12}$ cycloalkyl, —N—($C_{1-12}$ alkyl)$_2$, —$C_{6-20}$ aryl, —$C_{6-20}$ aryl-$C_{1-12}$ alkyl, —$C_{6-20}$ aryl-O—$C_{1-12}$ alkyl, —$C_{3-20}$ heteroaryl, —$C_{3-20}$ heteroaryl-$C_{1-12}$ alkyl, —$C_{3-20}$ heteroaryl-O—$C_{1-12}$ alkyl, —COOH, —OH, —SO$_3$H, —NH$_2$, and halogen.

In some embodiments, the aryl bidentate phosphine ligand has a structural formula represented by formulas a-x:

formula a

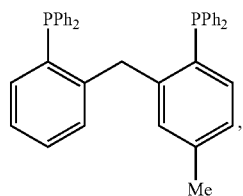

formula b

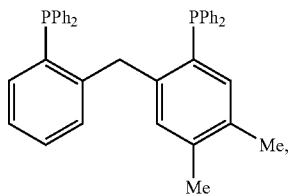

formula c

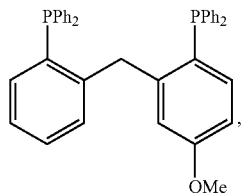

formula e

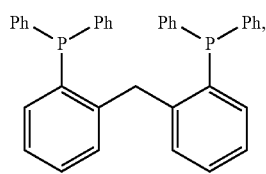

formula f

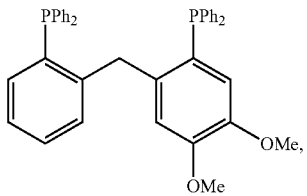

formula g

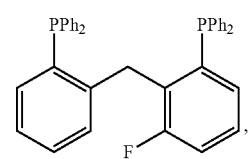

formula h

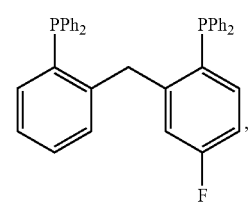

formula i

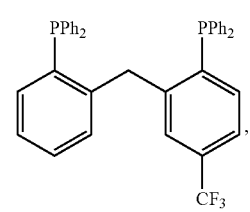

formula j

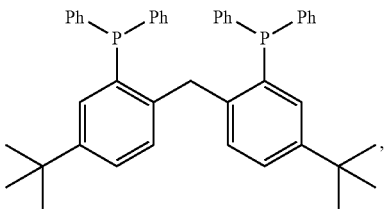

formula m

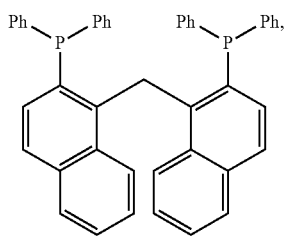

formula r

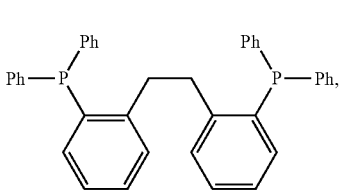

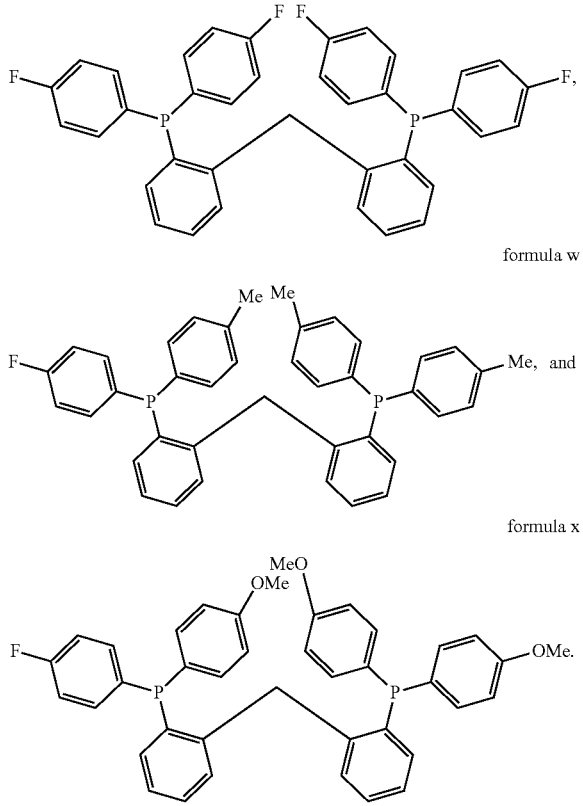

formula u formula w formula x

In some embodiments, the palladium compound is one selected from the group consisting of palladium acetate, palladium chloride, bis(triphenylphosphine) palladium dichloride, bis(acetonitrile) palladium dichloride, (1,5-cyclooctadiene) palladium dichloride, allylpalladium chloride, tetrakis(triphenylphosphine)palladium, palladium acetylacetonate, bis(dibenzylideneacetone) palladium, and tris(dibenzylideneacetone) dipalladium.

In some embodiments, the acidic additive is one selected from the group consisting of perchloric acid, sulfuric acid, phosphoric acid, hydrochloric acid, formic acid, acetic acid, oxalic acid, methanesulfonic acid, trifluoromethanesulfonic acid, tert-butane-sulfonic acid, p-toluenesulfonic acid, 2-hydroxy-propane-2-sulfonic acid, 2,4,6-trimethylbenzenesulfonic acid, dodecyl sulfonic acid, and aluminum trifluoromethanesulfonate.

In some embodiments, the terminal olefin is an olefin having 2-20 carbon atoms.

In some embodiments, the olefin having 2-20 carbon atoms is one or more selected from the group consisting of ethylene, propylene, 1-butene, cis-2-butene, trans-2-butene, isobutene, 1,3-butadiene, 1-pentene, cis-2-pentene, trans-2-pentene, 2-methyl-1-butene, 3-methyl-1-butene, 2-methyl-2-butene, hexene, tetramethylethylene, heptene, 1-octene, 2-octene, di-n-butene, diisobutene, n-decene, dodecene, hexadecene, and octadecene.

In some embodiments, the amount of the combined catalyst is based on the amount of the palladium compound relative to the amount of the terminal olefin: the molar amount of the palladium compound is 0.001-5% of the molar amount of the terminal olefin.

In some embodiments, the amount of the combined catalyst is based on the amount of the palladium compound relative to the amount of the terminal olefin: the molar amount of the palladium compound is 0.05-1% of the molar amount of the terminal olefin.

In some embodiments, the alcohol is an aliphatic alcohol compound or a cycloaliphatic alcohol compound containing 1-20 carbon atoms.

In some embodiments, the alcohol is one or more selected from the group consisting of methanol, ethanol, 1-propanol, isopropanol, isobutanol, tert-butanol, 1-butanol, 2-butanol, 1-pentanol, 2-pentanol, 3-pentanol, 1-hexanol, cyclohexanol, 2-ethylhexanol, isononanol, 2-propylheptanol, cyclohexane-1,2-diol, 1,2-ethylene glycol, 1,3-propylene glycol, glycerol, 1,2,4-butanetriol, 2-hydroxymethyl-1,3-propanediol, pentaerythritol, 1,2,6-trihydroxyhexane, and 1,1,1-tris(hydroxymethyl) ethane.

In some embodiments, the organic solvent is one selected from the group consisting of alcohol, dioxane, tetrahydrofuran, 1,2-ethanediol dimethyl ether, tetraglyme, 1,2-diethoxyethyl ether, ethyl acetate, butyl acetate, benzene, toluene, anisole, xylene, dichloromethane, trichloromethane, and chloroform.

In some embodiments, under the condition that the organic solvent is an alcohol, a molar ratio of the terminal olefin to the organic solvent ranges from 1:1 to 1:50.

In some embodiments, the hydroesterification reaction is performed at a pressure of 0.5-10.0 MPa and a temperature of 30-180° C.

In some embodiments, the hydroesterification reaction is performed at a pressure of 3-6 MPa and a temperature of 80-120° C.

DETAILED DESCRIPTION

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

The present disclosure provides a method for preparing an organic carboxylic ester by a combined catalyst of an aryl bidentate phosphine ligand comprising
subjecting a terminal olefin, carbon monoxide and an alcohol to a hydroesterification reaction in an organic solvent in the presence of a combined catalyst of a palladium compound, an aryl bidentate phosphine ligand, and an acidic additive, to generate an organic carboxylic ester having one more carbon atom than the terminal olefin.

In some embodiments of the present disclosure, the hydroesterification reaction is performed at a pressure of 0.5-10.0 MPa and preferably at 3-6 MPa. In some embodiments, the hydroesterification reaction is performed at a temperature of 30-180° C. and preferably at 80-120° C.

In some embodiments of the present disclosure, in the combined catalyst of a palladium compound, an aryl bidentate phosphine ligand, and an acidic additive, a molar ratio of the aryl bidentate phosphine ligand to the palladium compound ranges from 0.1:1 to 100:1 and preferably from 2:1 to 10:1. In some embodiments, a molar ratio of the acidic additive to the palladium compound ranges from 0.1:1 to 100:1 and preferably from 2:1 to 20:1. In some embodiments, the amount of the combined catalyst is based on the amount of the palladium compound relative to the amount of the terminal olefin: the molar amount of the palladium compound is 0.001-5% of the molar amount of the terminal olefin and preferably 0.05-1%.

In the present disclosure, in the combined catalyst of a palladium compound, an aryl bidentate phosphine ligand, and an acidic additive, the aryl bidentate phosphine ligand has a structural formula of

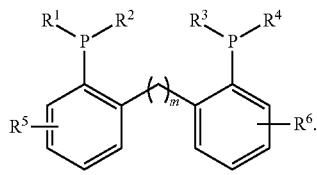

Here, m is 1 or 2.

Each of $R^1$, $R^2$, $R^3$ and $R^4$ is independently selected from the group consisting of $C_6$-$C_{20}$ aryl, $C_3$-$C_{20}$ heteroaryl, substituted $C_6$-$C_{20}$ aryl, and substituted $C_3$-$C_{20}$ heteroaryl. In the substituted $C_{6-20}$ aryl and substituted $C_{3-20}$ heteroaryl, a substituent is selected from the group consisting of —$C_{1-12}$ alkyl, —$C_{3-12}$ cycloalkyl, —$C_{3-12}$ heterocycloalkyl, —$C_{6-20}$ aryl, —$C_{3-20}$ heteroaryl, —O—$C_{1-12}$ alkyl, —O—$C_{1-12}$ alkyl-$C_{6-20}$ aryl, —O—$C_{3-12}$ cycloalkyl, —S—$C_{1-12}$ alkyl, —S—$C_{3-12}$ cycloalkyl, —COO—$C_{1-12}$ alkyl, —COO—$C_{3-12}$ cycloalkyl, —CONH—$C_{1-12}$ alkyl, —CONH—$C_{3-12}$ cycloalkyl, —CO—$C_{1-12}$ alkyl, —CO—$C_{3-12}$ cycloalkyl, —N—($C_{1-12}$ alkyl)$_2$, —$C_{6-20}$ aryl, —$C_{6-20}$ aryl-$C_{1-12}$ alkyl, —$C_{6-20}$ aryl-O—$C_{1-12}$ alkyl, —$C_{3-20}$ heteroaryl, —$C_{3-20}$ heteroaryl-$C_{1-12}$ alkyl, —$C_{3-20}$ heteroaryl-O—$C_{1-12}$ alkyl, —COOH, —OH, —SO$_3$H, —NH$_2$, and halogen.

Each of $R^5$ and $R^6$ is independently selected from the group consisting of hydrogen, $C_{1-18}$ alkyl, methoxy, phenyl, phenoxy, halogen, trifluoromethyl, cyano, and nitro.

In some embodiments of the present disclosure, the palladium compound is one selected from the group consisting of palladium acetate, palladium chloride, bis(triphenylphosphine) palladium dichloride, bis(acetonitrile) palladium dichloride, (1,5-cyclooctadiene) palladium dichloride, allylpalladium chloride, tetrakis(triphenylphosphine)palladium, palladium acetylacetonate, bis(dibenzylideneacetone) palladium, and tris(dibenzylideneacetone) dipalladium. The palladium compound may preferably be PdCl$_2$, Pd(acac)$_2$, bis(acetonitrile) palladium dichloride, (1,5-cyclooctadiene) palladium dichloride, or allylpalladium chloride.

In some embodiments of the present disclosure, the acidic additive is one selected from the group consisting of perchloric acid, sulfuric acid, phosphoric acid, hydrochloric acid, formic acid, acetic acid, oxalic acid, methanesulfonic acid, trifluoromethanesulfonic acid, tert-butanesulfonic acid, p-toluenesulfonic acid (PTSA), 2-hydroxy-propane-2-sulfonic acid, 2,4,6-trimethylbenzenesulfonic acid, dodecyl sulfonic acid, and aluminum trifluoromethanesulfonate. The acidic additive may preferably be p-toluenesulfonic acid, methanesulfonic acid, trifluoromethanesulfonic acid, tert-butane-sulfonic acid, 2,4,6-trimethylbenzenesulfonic acid, or dodecylsulfonic acid.

In some embodiments of the present disclosure, the terminal olefin having 2-20 carbon atoms is one or more selected from the group consisting of ethylene, propylene, 1-butene, cis-2-butene, trans-2-butene, isobutene, 1,3-butadiene, 1-pentene, cis-2-pentene, trans-2-pentene, 2-methyl-1-butene, 3-methyl-1-butene, 2-methyl-2-butene, hexene, tetramethylethylene, heptene, 1-octene, 2-octene, di-n-butene, diisobutene, n-decene, dodecene, hexadecene, and octadecene.

In some embodiments of the present disclosure, the alcohol is an aliphatic alcohol compound or a cycloaliphatic alcohol compound containing 1-20 carbon atoms, preferably one or more selected from the group consisting of methanol, ethanol, 1-propanol, isopropanol, isobutanol, tert-butanol, 1-butanol, 2-butanol, 1-pentanol, 2-pentanol, 3-pentanol, 1-hexanol, cyclohexanol, 2-ethylhexanol, isononanol, 2-propylheptanol, cyclohexane-1,2-diol, 1,2-ethylene glycol, 1,3-propylene glycol, glycerol, 1,2,4-butanetriol, 2-hydroxymethyl-1,3-propanediol, pentaerythritol, 1,2,6-trihydroxyhexane, and 1,1,1-tris(hydroxymethyl) ethane.

In some embodiments of the present disclosure, the organic solvent is one selected from the group consisting of alcohol, dioxane, tetrahydrofuran, 1,2-ethanediol dimethyl ether, tetraglyme, 1,2-diethoxyethyl ether, ethyl acetate, butyl acetate, benzene, toluene, anisole, xylene, dichloromethane, trichloromethane, and chloroform. Under the condition that the organic solvent is an alcohol, the alcohol acts as a reactant and meanwhile as an organic solvent. Under the condition that the organic solvent is an alcohol, a molar ratio of the terminal olefin to the organic solvent ranges from 1:1 to 1:50.

The method for preparing an organic carboxylic ester by a combined catalyst of an aryl bidentate phosphine ligand according to the present disclosure will be further illustrated below through specific examples.

Example 1. Preparation of Methyl Propionate (1) Preparation of Aryl Bidentate Phosphine Ligand
a (bis(2-(diphenylphosphino)phenyl)methane)

The preparation of bis(2-bromophenyl)methanol: 14.0 g of a solution of 2-bromoiodobenzene (50 mmol) in tetrahydrofuran (250 mL) was added slowly and dropwise to an isopropyl magnesium chloride-lithium chloride solution (2 M in THF, 27 mL, 54 mmol) under argon atmosphere at −15° C. When the exchange was completed, the reaction solution was cooled to −78° C., and 2-bromobenzaldehyde was added thereto. After the addition was completed, the reaction temperature was raised to room temperature and the mixture was stirred for 24 h. After the reaction was completed, the reaction was quenched by adding hydrochloric acid (6 M). The resulting mixture was subjected to an extraction with ethyl acetate (3×80 mL), and the obtained organic phase was dried with anhydrous sodium sulfate. The solvent therein was distilled off under reduced pressure. The resulting mixture was purified by silica gel chromatography, obtaining 15.39 g of bis(2-bromophenyl) methanol (45 mmol, 90%).

$^1$H NMR (400 MHz, CDCl$_3$): δ=7.59 (d, J=6 Hz, 2H), 7.33 (m, 4H), 7.18 (m, 2H), 6.42 (s, 1H), 2.59 (s, 1H).

$^{13}$C NMR (100 MHz, CDCl$_3$): δ 141.1, 133.2, 129.6, 128.9, 127.8, 124.1, 74.4.

Preparation of bis(2-bromophenyl)methane:hydroiodic acid (25.8 mL, 57% aqueous solution, 196 mmol) was added to 16.8 g of a solution of bis(2-bromophenyl) methanol (49.1 mmol) in acetic acid (250 mL) at room temperature. The resulting mixture was reacted at 130° C. for 2 h, and then cooled to room temperature. Then, a saturated NaSO$_3$ solution and water were added thereto, and the resulting mixture was subjected to an extraction with ethyl acetate (3×80 mL). The obtained organic phase was dried with anhydrous sodium sulfate, and the solvent was distilled off under reduced pressure. The resulting mixture was purified by silica gel column chromatography, obtaining 11.2 g of bis(2-bromophenyl) methane (70%).

$^1$H NMR (400 MHz, CDCl$_3$): δ=7.60 (dd, J=8.0, J=1.3, 2H), 7.22 (m, 2H), 7.11 (m, 2H), 6.98 (dd, J=7.6, 1.6, 2H), 4.20 (s, 2H).

$^{13}$C NMR (100 MHz, CDCl$_3$): δ=138.9, 132.8, 130.7, 128.1, 127.5, 125.1, 42.1. 151.4, 136.0, 130.3, 129.7, 124.8, 124.6, 41.0.

Preparation of bis(2-(diphenylphosphino)phenyl)methane: 3.26 g of bis(2-bromophenyl) methane (10 mmol) was added into a 100 mL Shrek flask and the atmosphere therein was replaced with an argon atmosphere. 30 mL of anhydrous ether was added thereto. After the resulting mixture was cooled to −78° C., 9.2 mL (22 mmol) of butyl lithium (2.4 M in n-hexane) was added slowly and dropwise thereto. The temperature was maintained at −78° C., and the mixture was stirred for 1 h and 4.84 g of diphenylphosphine chloride (22 mmol) was added thereto. The temperature was raised to room temperature, and the resulting mixture was reacted at room temperature for 24 h. The reaction was quenched by adding water, and the resulting mixture was subjected to an extraction with dichloromethane. The obtained organic phase was dried with anhydrous sodium sulfate, and the solvent was distilled off under reduced pressure. The resulting mixture was purified by silica gel chromatography, obtaining 4.020 g of bis(2-(diphenylphosphino)phenyl) methane (75%)

$^1$H NMR (400 MHz, CD$_3$COCD$_3$): δ=4.45 (d, J=2.0 Hz, 2H), 6.87-7.36 (m, 28H).

$^{31}$P NMR (162 MHz, CD$_3$COCD$_3$): δ−11.5.

The synthetic route of aryl bidentate phosphine ligand a (bis(2-(diphenylphosphino)phenyl)methane) was as follows:

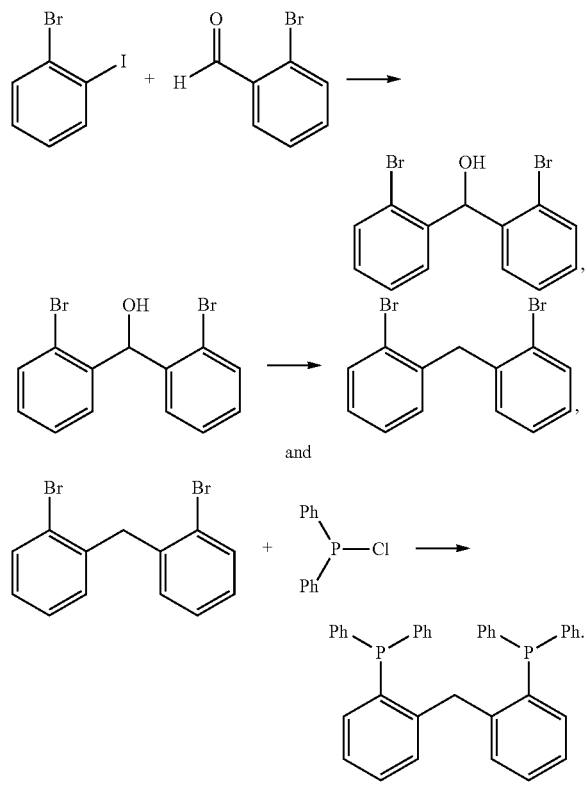

(2) Preparation of methyl propionate: Pd(acac)$_2$ (0.03 mmol), aryl bidentate phosphine ligand a (0.06 mmol), p-toluenesulfonic acid (0.12 mmol), and anhydrous methanol (10 mL) were added into a 100 ml autoclave. After the autoclave was sealed, the atmosphere therein was replaced with carbon monoxide for 3 times, then 2 g of ethylene (66.7 mmol) was charged thereto, and then carbon monoxide was charged thereto until the pressure in the autoclave was 5.0 MPa. The temperature was slowly raised to 100° C. by means of a temperature controller, and the resulting mixture was reacted at this temperature for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of ethylene was 90%, and the selectivity of methyl propionate was 96%.

Example 2. Preparation of Methyl Propionate (1) Preparation of aryl bidentate phosphine ligand c: The preparation method was the same as that of the aryl bidentate phosphine ligand a, except that 2-bromobenzaldehyde was replaced with 2-bromo-5-fluorobenzaldehyde. The aryl bidentate phosphine ligand c had a structural formula of

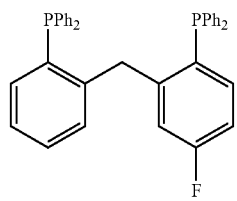

(2) Preparation of methyl propionate: The preparation method was the same as described in Example 1, except that aryl bidentate phosphine ligand c was used. The conversion rate of ethylene was 83%, and the selectivity of methyl propionate was 98%.

Example 3. Preparation of Methyl Propionate (1) Preparation of aryl bidentate phosphine ligand e: The preparation method was the same as that of aryl bidentate phosphine ligand a, except that 2-bromobenzaldehyde was replaced with 2-bromo-5-trifluoromethylbenzaldehyde. The aryl bidentate phosphine ligand e had a structural formula of

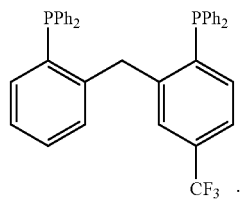

(2) Preparation of methyl propionate: The preparation method was the same as described in Example 1, except that aryl bidentate phosphine ligand e was used. The conversion rate of ethylene was 79%, and the selectivity of methyl propionate was 97%.

Example 4. Preparation of Methyl Propionate (1) Preparation of aryl bidentate phosphine ligand g: The preparation method was the same as that of aryl bidentate phosphine ligand a, except that 2-bromobenzaldehyde was replaced with 2-bromo-4,5-dimethylbenzaldehyde. The aryl bidentate phosphine ligand g had a structural formula of

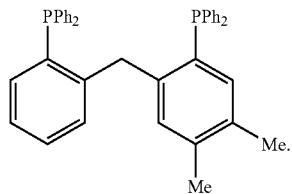

(2) Preparation of methyl propionate: The preparation method was the same as described in Example 1, except that aryl bidentate phosphine ligand g was used. The conversion rate of ethylene was 98%, and the selectivity of methyl propionate was 99%.

Example 5. Preparation of Methyl Propionate (1) Preparation of aryl bidentate phosphine ligand i: The preparation method was the same as that of aryl bidentate phosphine ligand a, except that 2-bromobenzaldehyde was replaced with 2-bromo-4,5-dimethoxybenzaldehyde. The aryl bidentate phosphine ligand i had a structural formula of

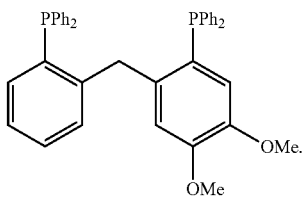

(2) Preparation of methyl propionate: The preparation method was the same as described in Example 1, except that aryl bidentate phosphine ligand i was used. The conversion rate of ethylene was 94%, and the selectivity of methyl propionate was 96%.

Example 6. Preparation of Methyl Propionate (1) Preparation of aryl bidentate phosphine ligand j (bis (4-(tert-butyl)$_2$-(diphenylphosphino)phenyl)methane):

The preparation of bis(2-bromo-(4-tert-butyl)phenyl) methane: 20.0 g of bis(4-tert-butylphenyl)methane (72 mmol), 0.36 g of iron powder (6.4 mmol), and dichloromethane (72 mL) were added in a 200 mL round bottom flask. A solution of bromine (7.7 mL, 150 mmol) in dichloromethane (36 mL) was added slowly thereto at 0° C. The temperature was raised to room temperature and the resulting mixture was reacted for 1 h. A NaHSO$_3$ solution was added thereto, and the mixture was subjected to an extraction with dichloromethane. The organic phase was dried with anhydrous sodium sulfate, and the solvent therein was distilled off under reduced pressure. The resulting mixture was purified by a silica gel chromatography, obtaining 29.959 g of bis(2-bromo-(4-tert-butyl)phenyl)methane (95%).

$^1$H NMR (400 MHz, CDCl$_3$): δ=7.59 (d, J=2.0 Hz, 2H), 7.23 (dd, J=2.0 Hz, J=8.1 Hz, 2H), 6.92 (d, J=8.1 Hz, 2H), 4.13 (s, 2H), 1.30 (s, 18H).

$^{13}$C NMR (100 MHz, CDCl$_3$): δ=151.4, 136.0, 130.3, 129.7, 124.8, 124.6, 41.0, 34.5, 31.2.

Preparation of bis(4-(tert-butyl)$_2$-(diphenylphosphino) phenyl)methane: 4.38 g of bis(2-bromo-4-(tert-butylphenyl))methane (10 mmol) was added into a 100 mL Shrek flask and the atmosphere therein was replaced with an argon atmosphere. 30 mL of anhydrous ether was added thereto. After the temperature was dropped to −78° C., 9.2 mL (22 mmol) of butyl lithium (2.4 M in n-hexane) was added slowly and dropwise thereto. The temperature was maintained at −78° C., and the resulting mixture was stirred for 1 h and 4.84 g of diphenylphosphine chloride (22 mmol) was added thereto. The temperature was then raised to room temperature and the resulting mixture was reacted for 24 h. The reaction was quenched by adding water, and the resulting mixture was subjected to an extraction with dichloromethane. The obtained organic phase was dried with anhydrous sodium sulfate, and the solvent therein was distilled off under reduced pressure. The resulting mixture was purified by silica gel chromatography, obtaining 4.536 g of bis(4-(tert-butyl)-2-(diphenylphosphino)phenyl)methane (70%).

$^1$H NMR (400 MHz, C$_6$D$_6$): δ=1.10 (s, 18H), 4.84 (t, J=2.2 Hz, 2H), 7.00-7.08 (m, 12H), 7.08-7.11 (m, 4H), 7.25 (m, 2H), 7.41 (m, 8H).

$^{13}$C NMR (100 MHz, C$_6$D$_6$): δ=30.9, 34.2, 37.8, 125.8, 128.3, 130.1, 130.8, 134.0, 136.0, 137.6, 142.9, 148.5.

$^{31}$P NMR (162 MHz, C$_6$D$_6$): δ=−13.3.

The synthetic route of aryl bidentate phosphine ligand j (bis(4-(tert-butyl)$_2$-(diphenylphosphino)phenyl)methane) was as follows:

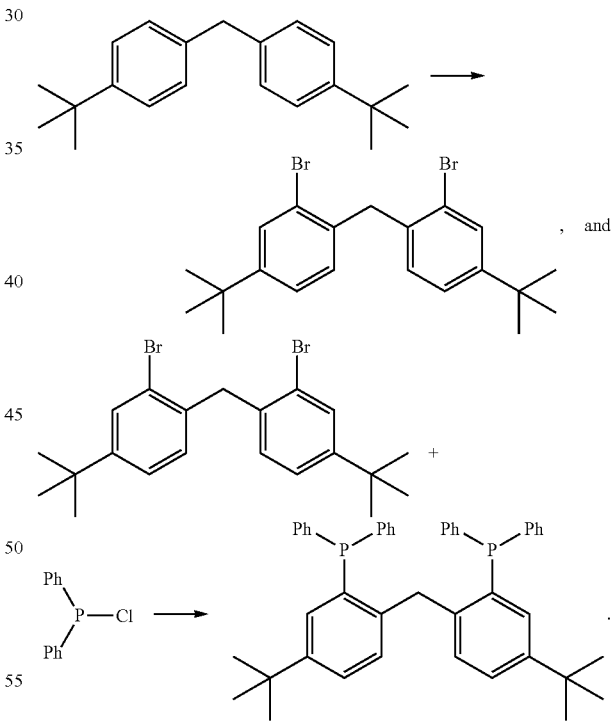

(2) Preparation of methyl propionate: The preparation method was the same as described in Example 1, except that aryl bidentate phosphine ligand j was used. The conversion rate of ethylene was 68%, and the selectivity of methyl propionate was 97%.

Example 7. Preparation of Methyl Propionate (1) Preparation of aryl bidentate phosphine ligand m (bis(2-(diphenylphosphino)naphthyl)methane)): Under argon atmosphere, 389.2 mg of bis(2-trifluoromethane-sulfonate-naphthyl)methane (0.69 mmol), 100.0 mg of sodium tert-butoxide (1.4 mmol), 8.0 mg of palladium acetate (0.036 mmol), 1,1'-bis(diphenylphosphine)ferrocene (20.0 mg, 0.036 mmol), 3 mL of toluene and 260.4 mg of diphenylphosphine (1.4 mmol) were added to a 100 mL Shrek flask in sequence. The resulting mixture was reacted at 110° C. for 24 h. The reaction was stopped and the resulting mixture was cooled to room temperature. The resulting mixture was filtered through celite, and the filtrate was washed with dichloromethane. After the crude product was concentrated, and then purified by silica gel chromatography, obtaining 445.9 mg of bis(2-(diphenylphosphino)naphthyl)methane (70%).

$^1$H NMR (400 MHz, CDCl$_3$) δ=8.11 (d, J=8.7 Hz, 2H), 7.63 (d, J=8.1 Hz, 2H), 7.56 (d, J=8.7 Hz, 2H), 7.31-7.10 (m, 24H), 7.07 (t, J=8.4 Hz, 2H), 6.76 (t, J=7.5 Hz, 2H).

$^{13}$C NMR (100 MHz, CDCl$_3$) δ=144.8, 144.6, 144.4, 136.9, 136.8, 134.2, 133.8, 133.5, 132.9, 130.2, 128.5, 128.3, 126.9, 126.0, 125.5, 36.0.

$^{31}$P NMR (162 MHz, CDCl$_3$) δ=−12.16.

The synthetic route of aryl bidentate phosphine ligand m (bis(2-(diphenylphosphino)naphthyl)methane) was as follows:

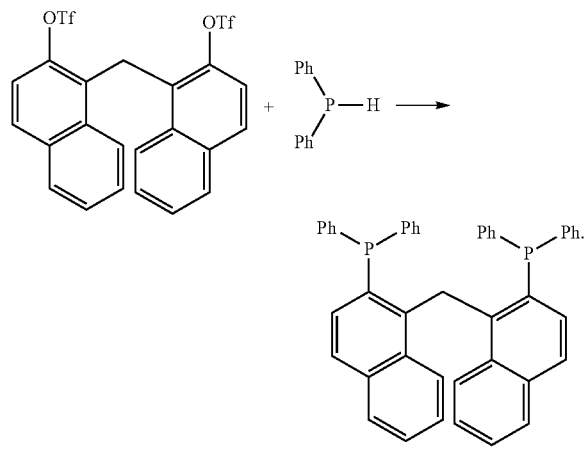

(2) Preparation of methyl propionate: The preparation method was the same as described in Example 1, except that aryl bidentate phosphine ligand m was used. The conversion rate of ethylene was 85%, and the selectivity of methyl propionate was 98%.

Example 8. Preparation of Methyl Propionate (1) Preparation of aryl bidentate phosphine ligand o: The preparation method was the same as that of aryl bidentate phosphine ligand a, except that 2-bromobenzaldehyde was replaced with 3-bromofuran-2-carbaldehyde. The aryl bidentate phosphine ligand o had a structural formula of

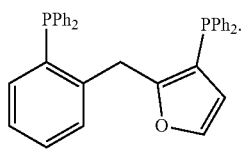

(2) Preparation of methyl propionate: The preparation method was the same as described in Example 1, except that aryl bidentate phosphine ligand o was used. The conversion rate of ethylene was 91%, and the selectivity of methyl propionate was 95%.

Example 9. Preparation of Methyl Propionate (1) Preparation of Aryl Bidentate Phosphine Ligand r (1,2-bis(2-(diphenylphosphino)phenyl)ethane)

Preparation of 1,2-bis(2-(bromophenyl)ethane: 33.36 g of 2-bromobenzyl bromide (133.5 mmol) was added into a 100 mL Shrek flask and the atmosphere was replaced with an argon atmosphere. 200 mL of tetrahydrofuran was added thereto. After being cooled to −78° C., 47.0 mL (66.7 mmol) of butyl lithium (1.4 M in n-hexane) was added slowly and dropwise thereto. The temperature was maintained at −78° C., and the resulting mixture was stirred for 3 h. The temperature was gradually raised to room temperature. The reaction was then quenched by adding water (40 mL), and the resulting mixture was subjected to an extraction with dichloromethane (3×50 mL). The resulting organic phase was dried with anhydrous sodium sulfate, and the solvent therein was distilled off under reduced pressure. The obtained white solid was recrystallized in hot hexane, obtaining 18.48 g of 1,2-bis(2-(bromophenyl)ethane (81%).

$^1$H NMR (400 MHz, CDCl$_3$) δ=7.55 (dd, J=7.8, 1.1 Hz, 2H), 7.24-7.17 (m, 4H), 7.07 (ddd, J=8.0, 6.7, 2.4 Hz, 2H), 3.05 (s, 4H).

$^{13}$C NMR (100 MHz, CDCl$_3$) δ=140.54, 132.77, 130.60, 127.79, 127.41, 124.46, 36.42.

Preparation of 1,2-bis(2-(diphenylphosphino)phenyl)ethane: 3.40 g of 1,2-bis(2-(bromophenyl) ethane (10 mmol) was added into a 100 mL Shrek flask and the atmosphere was replaced with an argon atmosphere. 30 mL of anhydrous ether was added thereto. After being cooled to −78° C., 9.2 mL (22 mmol) of butyl lithium (2.4 M in n-hexane) was added slowly and dropwise thereto. The temperature was maintained at −78° C., and the mixture was stirred for 1 h. Diphenylphosphine chloride (4.84 g, 22 mmol) was added thereto. The temperature was raised to room temperature and the resulting mixture was reacted for 24 h. The reaction was quenched by adding water, and the resulting mixture was subjected to an extraction with dichloromethane (3×50 mL). The obtained organic phase was dried with anhydrous sodium sulfate, and the solvent therein was distilled off under reduced pressure. The resulting mixture was purified by silica gel chromatography, obtaining 4.536 g of 1,2-bis (2-(diphenylphosphino)phenyl)ethane (70%).

$^1$H NMR (400 MHz, C$_6$D$_6$): δ=6.86-7.40 (m, 48H), 3.44 (s, 4H).

$^{13}$C NMR (100 MHz, C$_6$D$_6$): δ=147.1 (d, J=25.8 Hz), 137.8 (d, J=11.9 Hz), 136.0 (d, J=11.9 Hz), 134.4 (d, J=20.4 Hz), 126.78-134.22 (m), 37.2 (d, J=23.6 Hz).

$^{31}$PNMR (162 MHz, C$_6$D$_6$): δ=15.1.

The synthetic route of aryl bidentate phosphine ligand r (bis(2-(diphenylphosphino)phenyl)ethane) was as follows:

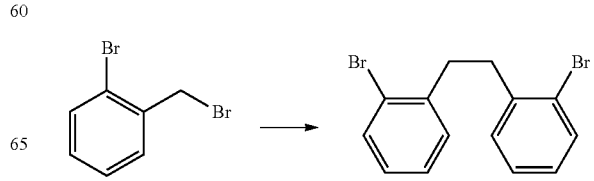

-continued

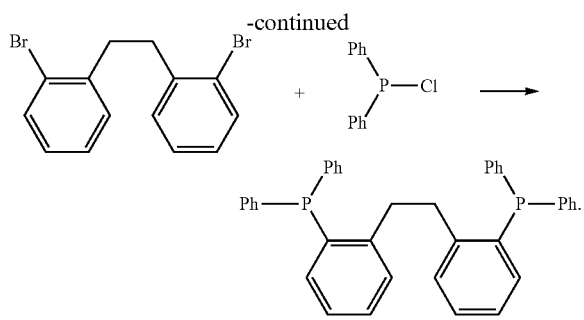

(2) Preparation of methyl propionate: The preparation method was the same as described in Example 1, except that aryl bidentate phosphine ligand r was used. The conversion rate of ethylene was 65%, and the selectivity of methyl propionate was 95%.

Example 10. Preparation of Methyl Propionate (1) Preparation of aryl bidentate phosphine ligand u: The preparation method was the same as that of aryl bidentate phosphine ligand a, except that chlorodiphenylphosphine was replaced with bis(4-fluorophenyl)chlorophosphine. The aryl bidentate phosphine ligand u had a structural formula of

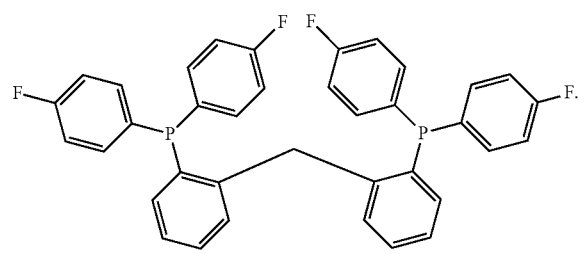 [SMILES: Fc1ccc(P(c2ccc(F)cc2)c2ccccc2Cc2ccccc2P(c2ccc(F)cc2)c2ccc(F)cc2)cc1]

(2) Preparation of methyl propionate: The preparation method was the same as described in Example 1, except that aryl bidentate phosphine ligand u was used. The conversion rate of ethylene was 80%, and the selectivity of methyl propionate was 96%.

Example 11. Preparation of Methyl Propionate (1) Preparation of aryl bidentate phosphine ligand w: The preparation method was the same as that of aryl bidentate phosphine ligand a, except that chlorodiphenylphosphine was replaced with chlorodi-p-tolylphosphane. The aryl bidentate phosphine ligand w had a structural formula of

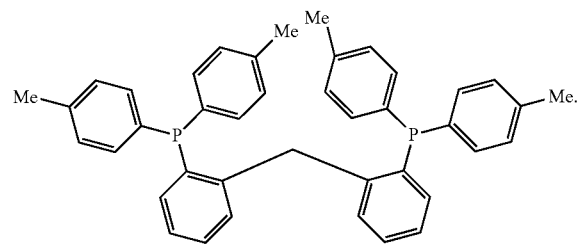 [SMILES: Cc1ccc(P(c2ccc(C)cc2)c2ccccc2Cc2ccccc2P(c2ccc(C)cc2)c2ccc(C)cc2)cc1]

(2) Preparation of methyl propionate: The preparation method was the same as described in Example 1, except that aryl bidentate phosphine ligand w was used. The conversion rate of ethylene was 97%, and the selectivity of methyl propionate was 98%.

Comparative Example 1. Preparation of Methyl Propionate (1) The comparative phosphine ligand 1,2-bis(di-tert-butylphosphinomethyl)benzene (DTBPMB) was available on the market. Its structural formula was as follows:

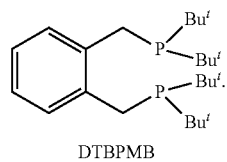

DTBPMB (2) Preparation of methyl propionate: The preparation method was the same as described in Example 1, except that the comparative phosphine ligand 1,2-bis(di-tert-butylphosphinomethyl)benzene was used. The conversion rate of ethylene was 97%, and the selectivity of methyl propionate was 99%.

Example 12. Preparation of Ethyl Propionate (1) Preparation of aryl bidentate phosphine ligand a: Aryl bidentate phosphine ligand a was prepared according to the method as described in Example 1.

(2) Preparation of ethyl propionate: Pd(acac)$_2$ (0.01 mmol), aryl bidentate phosphine ligand a (0.04 mmol), p-toluenesulfonic acid (0.1 mmol), and anhydrous ethanol (10 mL) were added to a 100 ml autoclave in sequence. After the autoclave was sealed, the atmosphere therein was replaced with carbon monoxide for 3 times. Ethylene (2 g, 66.7 mmol) was then charged thereto, and carbon monoxide was then charged thereto until the pressure in the autoclave was 4.0 MPa. The temperature was slowly raised to 100° C. by means of a temperature controller, and the mixture was reacted for 4 h. After being cooled to room temperature, the autoclave was slowly deflated, and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of ethylene was 90%, and the selectivity of ethyl propionate was 98%.

Example 13. Preparation of Propyl Propionate (1) Preparation of aryl bidentate phosphine ligand b: The preparation method was the same as that of aryl bidentate phosphine ligand a, except that 2-bromobenzaldehyde was replaced with 2-bromo-6-fluorobenzaldehyde. The aryl bidentate phosphine ligand b had a structural formula of

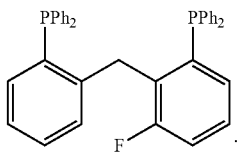

(2) Preparation of propyl propionate: Bis(triphenylphosphine)palladium dichloride (0.10 mmol), aryl bidentate phosphine ligand b (0.04 mmol), sulfuric acid (0.30 mmol), n-propanol (8 mL), and dioxane (5 mL) were added to a 100 ml autoclave in sequence. After the autoclave was sealed, the atmosphere therein was replaced with carbon monoxide for 3 times. Ethylene (2 g, 66.7 mmol) was charged thereto, and carbon monoxide was then charged thereto until the pressure in the autoclave was 5.0 MPa. The temperature was slowly raised to 90° C. by means of a temperature controller, and the resulting mixture was reacted for 8 h. After being cooled to room temperature, the autoclave was slowly deflated, and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of ethylene was 89%, and the selectivity of propyl propionate was 97%.

Example 14. Preparation of Octyl Propionate (1) Preparation of aryl bidentate phosphine ligand c: Aryl bidentate phosphine ligand c was prepared according to the method as described in Example 2.

(2) Preparation of octyl propionate: 0.50 mmol of bis(acetonitrile)palladium dichloride, 0.04 mmol of aryl bidentate phosphine ligand c, 0.5 mmol of phosphoric acid, and 10 mL of n-octanol were added to a 100 ml autoclave in sequence. After the autoclave was sealed, the atmosphere therein was replaced with carbon monoxide for 3 times. 1 g of ethylene (33.3 mmol) was charged, and carbon monoxide was then charged until the pressure in the autoclave was 8.0 MPa. The temperature was slowly raised to 60° C. by means of a temperature controller, and the resulting mixture was reacted for 4 h. After being cooled to room temperature, the autoclave was slowly deflated, and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of ethylene was 90%, and the selectivity of octyl propionate was 96%.

Example 15. Preparation of Lauryl Propionate (1) Preparation of aryl bidentate phosphine ligand f: The preparation method was the same as that of aryl bidentate phosphine ligand a, except that 2-bromobenzaldehyde was replaced with 2-bromo-5-methylbenzaldehyde. The aryl bidentate phosphine ligand f had a structural formula of

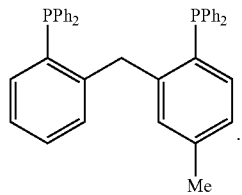

(2) Preparation of lauryl propionate: 0.01 mmol of Pd(acac)$_2$, 0.08 mmol of aryl bidentate phosphine ligand f, 0.4 mmol of hydrochloric acid, and 10 mL of n-dodecanol were added to a 100 ml autoclave in sequence. After the autoclave was sealed, the atmosphere was replaced with carbon monoxide for 3 times. 2 g of ethylene (66.7 mmol) was charged thereto, and carbon monoxide was charged thereto until the pressure in the autoclave was 4.0 MPa. The temperature was slowly raised to 100° C. by means of a temperature controller, and the resulting mixture was reacted for 4 h. After being cooled to room temperature, and the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of ethylene was 96%, and the selectivity of lauryl propionate was 96%.

Example 16. Preparation of Phenyl Propionate (1) Preparation of aryl bidentate phosphine ligand g: Aryl bidentate phosphine ligand g was prepared according to the method as described in Example 4.

(2) Preparation of phenyl propionate: 0.20 mmol of (1,5-cyclooctadiene)palladium dichloride, 0.04 mmol of aryl bidentate phosphine ligand g, 0.1 mmol of p-toluenesulfonic acid, 10 g of phenol, and 10 mL of toluene were added to a 100 ml autoclave in sequence. After the autoclave was sealed, the atmosphere was replaced with carbon monoxide for 3 times. 2 g of ethylene (66.7 mmol) was charged thereto, and carbon monoxide was then charged thereto until the pressure in the autoclave was 6.0 MPa. The temperature was slowly raised to 120° C. by means of a temperature controller, and the resulting mixture was reacted for 4 h. After being cooled to room temperature, and the autoclave was deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of ethylene was 98%, and the selectivity of phenyl propionate was 96%.

Example 17. Preparation of Methyl Butyrate and Methyl Isobutyrate (1) Preparation of aryl bidentate phosphine ligand i: Aryl bidentate phosphine ligand i was prepared according to the method as described in Example 5.

(2) Preparation of methyl butyrate and methyl isobutyrate: 0.30 mmol of Pd(acac)$_2$, 0.04 mmol of aryl bidentate phosphine ligand i, 0.1 mmol of methanesulfonic acid, 10 mL of anhydrous methanol, and 10 mL of 1,2-ethanediol dimethyl ether were added to a 100 ml autoclave in sequence. After the autoclave was sealed, the atmosphere was replaced with carbon monoxide for 3 times. 30 mmol of propylene was then charged thereto, and carbon monoxide was then charged thereto until the pressure in the autoclave was 4.0 MPa. The temperature was slowly raised to 100° C. by means of a temperature controller, and the mixture was reacted for 4 h. After being cooled to room temperature, and the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of propylene was 94%, and the selectivity of hydroesterification products (methyl butyrate and methyl isobutyrate) was 98% (methyl butyrate/methyl isobutyrate was 94/6). The reaction was performed according to the following equation:

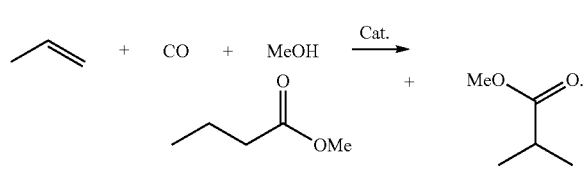

Example 18. Preparation of Methyl Butyrate and Methyl Isobutyrate (1) Preparation of aryl bidentate phosphine ligand j: Aryl bidentate phosphine ligand j was prepared according to the method as described in Example 6.

(2) Preparation of methyl butyrate and methyl isobutyrate: 0.01 mmol of allylpalladium chloride, 0.20 mmol of aryl bidentate phosphine ligand j, 0.1 mmol of p-toluenesulfonic acid, and 10 mL of anhydrous methanol were added to a 100 ml autoclave in sequence. After the autoclave was sealed, the atmosphere therein was replaced with carbon monoxide for 3 times. 66.7 mmol of propylene was then charged thereto, and then carbon monoxide was charged thereto until the pressure in the autoclave was 3.0 MPa. The temperature was slowly raised to 150° C. by means of a temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of propylene was 88%, and the selectivity of hydroesterification products (methyl butyrate, methyl isobutyrate) was 95% (methyl butyrate/methyl isobutyrate was 95/5). The reaction was performed according to the following equation:

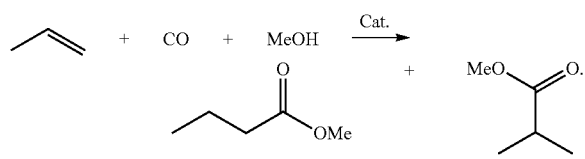

Example 19. Preparation of Methyl Valerate and Methyl Isovalerate (1) Preparation of aryl bidentate phosphine ligand g: Aryl bidentate phosphine ligand g was prepared according to the method as described in Example 4.

(2) Preparation of methyl valerate and methyl isovalerate: 0.5 mmol of palladium chloride, 0.04 mmol of aryl bidentate phosphine ligand g, 0.05 mmol of trifluoromethanesulfonic acid, 10 mL of anhydrous methanol, and 8 mL of ethyl acetate were added to a 100 ml autoclave in sequence. After the autoclave was sealed, the atmosphere therein was replaced with carbon monoxide for 3 times. 10 mmol of butene was then charged thereto, and carbon monoxide was then charged thereto until the pressure in the autoclave was 2.0 MPa. The temperature was slowly raised to 100° C. by means of a temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of butene was 98%, and the selectivity of hydroesterification products (methyl valerate and methyl isovalerate) was 97% (methyl valerate/methyl isovalerate was 97/3). The reaction was performed according to the following equation:

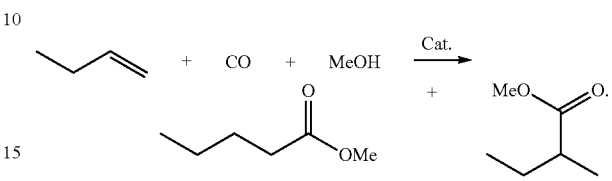

Example 20. Preparation of Methyl Heptanoate and Methyl Isoheptanoate (1) Preparation of aryl bidentate phosphine ligand h: The preparation method was the same as that of aryl bidentate phosphine ligand a, except that 2-bromobenzaldehyde was replaced with 2-bromo-5-methoxybenzaldehyde. The aryl bidentate phosphine ligand h had a structural formula of

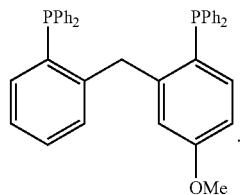

(2) Preparation of methyl heptanoate and methyl isoheptanoate: 0.05 mmol of Pd(acac)$_2$, 0.04 mmol of aryl bidentate phosphine ligand h, 0.1 mmol of tert-butane sulfonic acid, 30 mmol of 1-hexene, and 10 mL of anhydrous methanol were added to a 100 ml autoclave in sequence. After the autoclave was sealed, the atmosphere therein was replaced with carbon monoxide for 3 times. Carbon monoxide was charged thereto until the pressure in the autoclave was 1.0 MPa. The temperature was slowly raised to 180° C. by means of a temperature controller, and the mixture was reacted for 24 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of 1-hexene was 80%, and the selectivity of hydroesterification products (methyl heptanoate and methyl isoheptanoate) was 90% (methyl heptanoate/methyl isoheptanoate was 94/6). The reaction was performed according to the following equation:

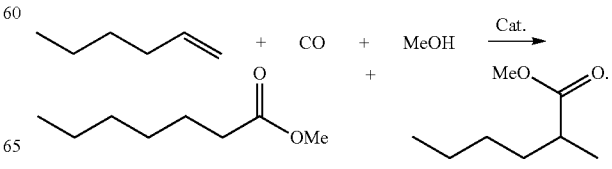

Example 21. Preparation of Methyl Nonanoate and Methyl 2-Methyloctanoate (1) Preparation of aryl bidentate phosphine ligand i: Aryl bidentate phosphine ligand i was prepared according to the method as described in Example 5.

(2) Preparation of methyl nonanoate and methyl 2-methyloctanoate: 0.20 mmol of tetratriphenylphosphine palladium, 0.04 mmol of aryl bidentate phosphine ligand i, 0.1 mmol of p-toluenesulfonic acid, 30 mmol of 1-octene, and 10 mL of anhydrous methanol were added to a 100 ml autoclave in sequence. After the autoclave was sealed, the atmosphere therein was replaced with carbon monoxide for 3 times, carbon monoxide was then charged thereto until the pressure in the autoclave was 4.0 MPa. The temperature was slowly raised to 100° C. by means of the temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of 1-octene was 96%, and the selectivity of hydroesterification products (methyl nonanoate and methyl 2-methyloctanoate) was 98% (methyl nonanoate/methyl 2-methyloctanoate was 94/6). The reaction was performed according to the following equation:

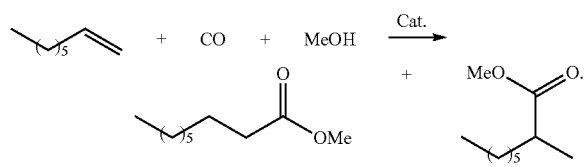

Example 22. Preparation of Methyl Tridecanoate/Methyl 2-Methyldodecanoate (1) Preparation of aryl bidentate phosphine ligand g: Aryl bidentate phosphine ligand g was prepared according to the method as described in Example 4.

(2) Preparation of methyl tridecanoate/methyl 2-methyldodecanoate: 0.30 mmol of Pd(acac)$_2$, 0.04 mmol of aryl bidentate phosphine ligand g, 0.1 mmol of 2-hydroxypropane-2-sulfonic acid, 30 mmol of 1-dodecene, and 10 mL of anhydrous methanol were added to a 100 ml autoclave in sequence. After the autoclave was sealed, the atmosphere was replaced with carbon monoxide for 3 times. Carbon monoxide was charged thereto until the pressure in the autoclave was 5.0 MPa. The temperature was slowly raised to 100° C. by means of a temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of 1-dodecene was 95%, and the selectivity of hydroesterification products (methyl tridecanoate and methyl 2-methyldodecanoate) was 96% (methyl tridecanoate/methyl 2-methyldodecanoate was 95/5). The reaction was prepared according to the following equation:

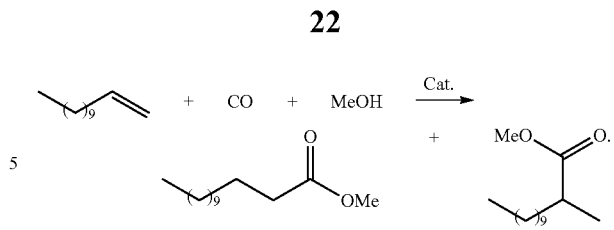

Example 23. Preparation of Methyl Phenylpropionate/Methyl 2-methylphenylacetate (1) Preparation of aryl bidentate phosphine ligand m: Aryl bidentate phosphine ligand m was prepared according to the method as described in Example 7.

(2) Preparation of methyl phenylpropionate/methyl 2-methylphenylacetate: 0.08 mmol of Pd(acac)$_2$, 0.04 mmol of aryl bidentate phosphine ligand m, 0.1 mmol of 2,4,6-trimethylbenzenesulfonic acid, 30 mmol of styrene, and 10 mL of anhydrous methanol were added to a 100 ml autoclave in sequence. After the autoclave was sealed, the atmosphere was replaced with carbon monoxide for 3 times, carbon monoxide was then charged thereto until the pressure in the autoclave was 6.0 MPa. The temperature was slowly raised to 80° C. by means of a temperature controller, and the mixture was reacted for 12 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of styrene was 90%, and the selectivity of hydroesterification products (methyl phenylpropionate and methyl 2-methylphenylacetate) was 95% (methyl phenylpropionate/methyl 2-methylphenylacetate was 96/4). The reaction was performed according to the following equation:

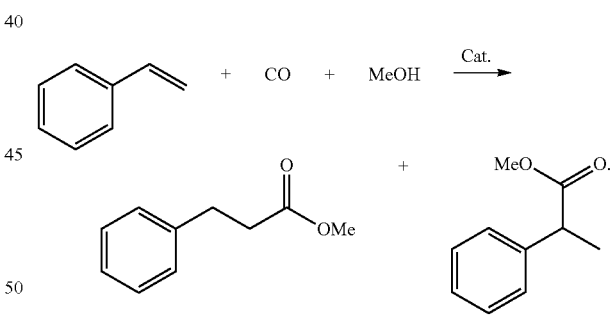

Example 24. Preparation of Phenyl Phenylpropionate/Phenyl 2-methylphenylacetate (1) Preparation of aryl bidentate phosphine ligand g: Aryl bidentate phosphine ligand g was prepared according to the method as described in Example 4.

(2) Preparation of phenyl phenylpropionate/phenyl 2-methylphenylacetate: 0.80 mmol of bis(dibenzylideneacetone) palladium, 0.10 mmol of aryl bidentate phosphine ligand g, 0.8 mmol of p-toluenesulfonic acid, 30 mmol of styrene, 10 g of phenol and 10 mL of anisole were added to a 100 ml autoclave in sequence. After the autoclave was sealed, the atmosphere was replaced with carbon monoxide for 3 times. Carbon monoxide was then charged thereto until the pressure in the autoclave was 4.0 MPa. The temperature was slowly raised to 100° C. by means of a temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of styrene was 95%, and the selectivity of hydroesterification products (phenyl phenylpropionate and phenyl 2-methylphenylacetate) was 95% (phenyl phenylpropionate/phenyl 2-methylphenylacetate was 97/3). The reaction was preformed according to the following equation:

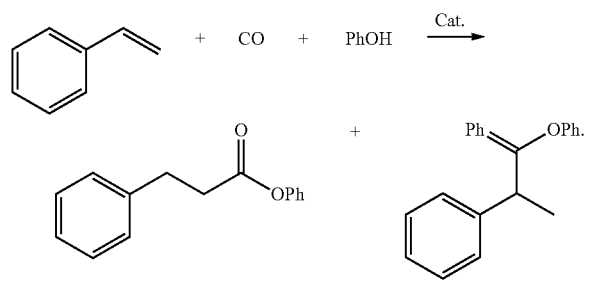

Example 25. Preparation of Ethyl 3-(4-methoxyphenyl)propionate/ethyl 2-(4-methoxyphenyl)propionate (1) Preparation of aryl bidentate phosphine ligand o: Aryl bidentate phosphine ligand o was prepared according to the method as described in Example 8.

(2) Preparation of ethyl 3-(4-methoxyphenyl)propionate/ethyl 2-(4-methoxyphenyl)propionate: 0.06 mmol of Pd(acac)$_2$, 0.30 mmol of aryl bidentate phosphine ligand o, 0.06 mmol of dodecyl sulfonic acid, 30 mmol of p-methoxystyrene, and 10 mL of anhydrous methanol were added to a 100 ml autoclave in sequence. After the autoclave was sealed, the atmosphere therein was replaced with carbon monoxide for 3 times. Carbon monoxide was then charged thereto until the pressure in the autoclave was 5.0 MPa. The temperature was slowly raised to 100° C. by means of a temperature controller, and the mixture was reacted for 8 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of p-methoxystyrene was 96%, and the selectivity of hydroesterification products (ethyl 3-(4-methoxyphenyl)propionate and ethyl 2-(4-methoxyphenyl)propionate) was 94% (ethyl 3-(4-methoxyphenyl)propionate/ethyl 2-(4-methoxyphenyl)propionate was 96/4). The reaction was performed according to the following equation:

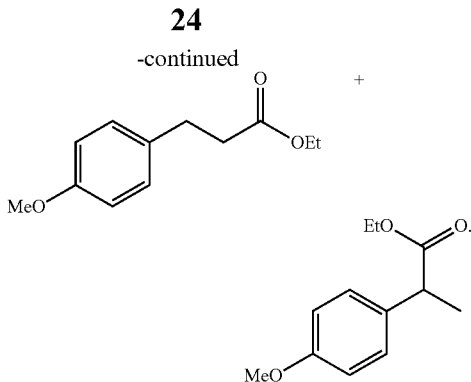

Example 26. Preparation of Ethyl 3-(4-methylphenyl)propionate/ethyl 2-(4-methylphenyl)propionate (1) Preparation of aryl bidentate phosphine ligand g: Aryl bidentate phosphine ligand g was prepared according to the method as described in Example 4.

(2) Preparation of ethyl 3-(4-methylphenyl)propionate/ethyl 2-(4-methylphenyl)propionate: 0.01 mmol of Pd(acac)$_2$, 0.04 mmol of aryl bidentate phosphine ligand g, 0.40 mmol of p-toluenesulfonic acid, 30 mmol of p-methylstyrene, 10 mL of anhydrous methanol, and 10 mL of xylene were added to a 100 ml autoclave in sequence. After the autoclave was sealed, the atmosphere therein was replaced with carbon monoxide for 3 times. Carbon monoxide was then charged thereto until the pressure in the autoclave was 6.0 MPa. The temperature was slowly raised to 100° C. by means of a temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of p-methylstyrene was 97%, and the selectivity of hydroesterification products (ethyl 3-(4-methylphenyl)propionate and ethyl 2-(4-methylphenyl)propionate) was 98% (ethyl 3-(4-methylphenyl)propionate/ethyl 2-(4-methylphenyl)propionate was 95/5). The reaction was performed according to the following equation:

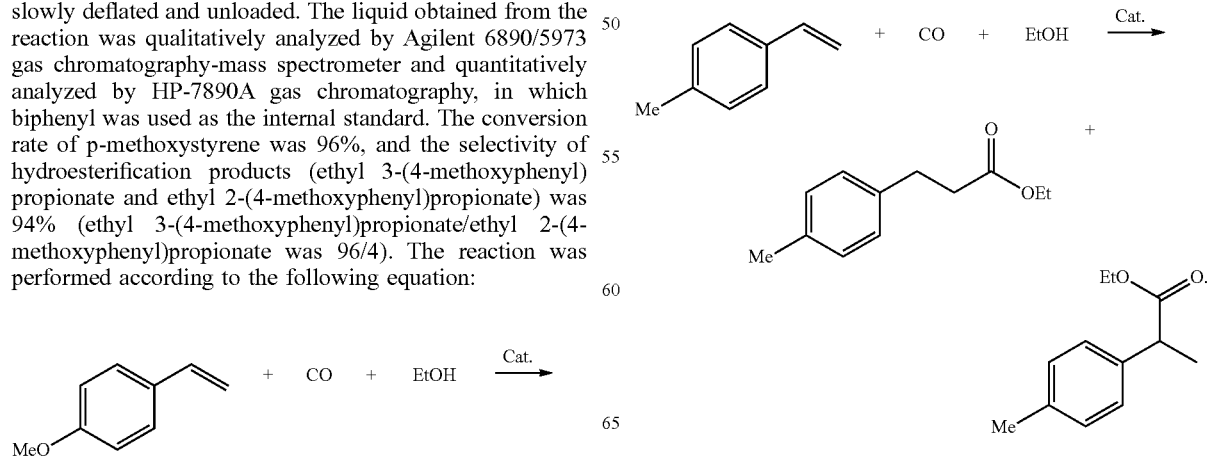

Example 27. Preparation of Isopropyl Phenylpropionate/Isopropyl 2-methylphenylacetate (1) Preparation of aryl bidentate phosphine ligand o: Aryl bidentate phosphine ligand o was prepared according to the method as described in Example 8.

(2) Preparation of isopropyl phenylpropionate/isopropyl 2-methylphenylacetate: 0.01 mmol of tris(dibenzylideneacetone) dipalladium, 1.0 mmol of aryl bidentate phosphine ligand o, 0.1 mmol of p-toluenesulfonic acid, 30 mmol of styrene, and 10 mL of anhydrous isopropanol were added to a 100 ml autoclave in sequence. After the autoclave was sealed, the atmosphere was replaced with carbon monoxide for 3 times. Carbon monoxide was then charged thereto until the pressure in the autoclave was 6.0 MPa. The temperature was slowly raised to 80° C. by means of a temperature controller, and the mixture was reacted for 16 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of styrene was 95%, and the selectivity of hydroesterification products (isopropyl phenylpropionate and isopropyl 2-methylphenylacetate) was 96% (isopropyl phenylpropionate/isopropyl 2-methylphenylacetate was 94/6). The reaction formula was performed according to the following equation:

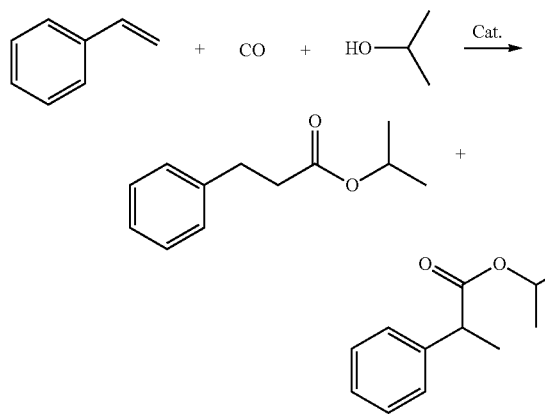

Example 28. Preparation of Ethyl 3-(4-fluorophenyl)propionate/ethyl 2-(4-fluorophenyl)propionate (1) Preparation of aryl bidentate phosphine ligand w: Aryl bidentate phosphine ligand w was prepared according to the method as described in Example 12.

(2) Preparation of ethyl 3-(4-fluorophenyl)propionate/ethyl 2-(4-fluorophenyl)propionate: 0.01 mmol of Pd(acac)$_2$, 0.20 mmol of aryl bidentate phosphine ligand w, 1.0 mmol of aluminum trifluoromethanesulfonate, 30 mmol of p-fluorostyrene, and 10 mL of ethanol were added to a 100 ml autoclave in sequence. After the autoclave was sealed, the atmosphere was replaced with carbon monoxide for 3 times. Carbon monoxide was then charged thereto until the pressure in the autoclave was 6.0 MPa. The temperature was slowly raised to 100° C. by means of a temperature controller, and the mixture was reacted for 20 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of p-fluorostyrene was 97%, and the selectivity of hydroesterification products (ethyl 3-(4-fluorophenyl)propionate and ethyl 2-(4-fluorophenyl)propionate) was 98% (ethyl 3-(4-fluorophenyl)propionate/ethyl 2-(4-fluorophenyl)propionate was 97/3). The reaction was performed according to the following equation:

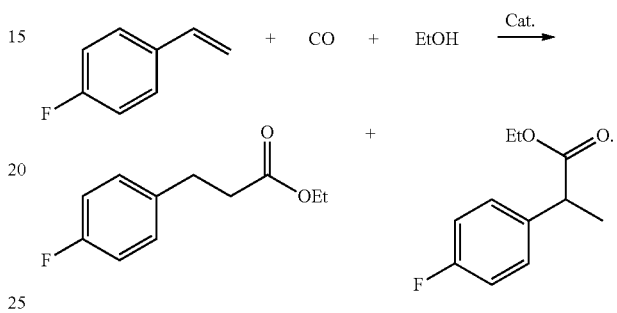

Example 29. Preparation of Ethyl 3-(4-bromophenyl)propionate/ethyl 2-(4-bromophenyl)propionate (1) Preparation of aryl bidentate phosphine ligand x: the preparation method was the same as that of the aryl bidentate phosphine ligand a, except that the chlorodiphenylphosphine was replaced with bis(4-methoxyphenyl)chlorophosphine, which had a structural formula of

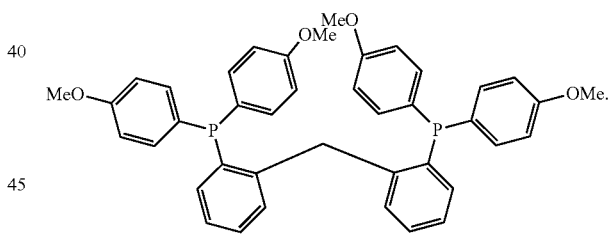

(2) Preparation of ethyl 3-(4-bromophenyl)propionate/ethyl 2-(4-bromophenyl)propionate: 0.01 mmol of allylpalladium chloride, 0.30 mmol of aryl bidentate phosphine ligand x, 0.30 mmol of p-toluenesulfonic acid, 30 mmol of p-bromostyrene, and 10 mL of ethanol were added to a 100 ml autoclave in sequence. After the autoclave was sealed, the atmosphere therein was replaced with carbon monoxide for 3 times. 30 mmol of p-bromostyrene was then charged thereto until the pressure in the autoclave was 8.0 MPa. The temperature was slowly raised to 100° C. by means of a temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of p-bromostyrene was 97%, and the selectivity of hydroesterification products (ethyl 3-(4-bromophenyl)propionate and ethyl 2-(4-bromophenyl)propionate) was 98% (ethyl 3-(4-bromophenyl)propionate/ethyl 2-(4-bromophenyl)propionate was 94/6). The reaction was performed according to the following equation:

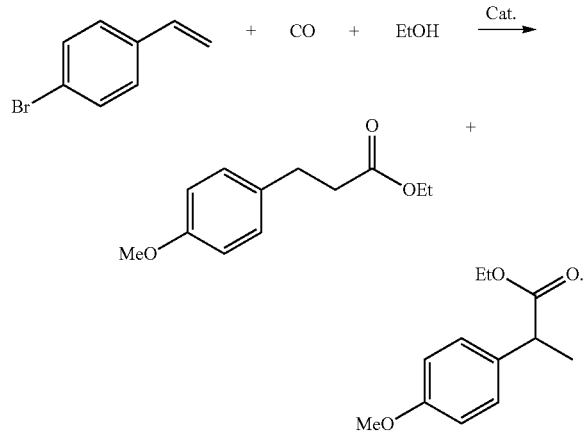

Example 30

(1) Preparation of aryl bidentate phosphine ligand w: Aryl bidentate phosphine ligand w was prepared according to the method as described in Example 12.

(2) Preparation of ethyl 3-(4-cyanophenyl)propionate/ethyl 2-(4-cyanophenyl)propionate: 0.01 mmol of Pd(acac)$_2$, 0.50 mmol of aryl bidentate phosphine ligand w, 0.50 mmol of p-toluenesulfonic acid, 30 mmol of p-cyanostyrene, 10 mL of ethanol, and 8 mL of chloroform were added to a 100 ml autoclave in sequence. After the autoclave was sealed, the atmosphere was replaced with carbon monoxide for 3 times. Carbon monoxide was then charged thereto until the pressure in the autoclave was 4.0 MPa. The temperature was slowly raised to 100° C. by means of a temperature controller, and the mixture was reacted for 4 h. After being cooled to room temperature, the autoclave was slowly deflated and unloaded. The liquid obtained from the reaction was qualitatively analyzed by Agilent 6890/5973 gas chromatography-mass spectrometer and quantitatively analyzed by HP-7890A gas chromatography, in which biphenyl was used as the internal standard. The conversion rate of p-cyanostyrene was 98%, and the selectivity of hydroesterification products (ethyl 3-(4-cyanophenyl)propionate and ethyl 2-(4-cyanophenyl)propionate) was 98% (ethyl 3-(4-cyanophenyl)propionate/ethyl 2-(4-cyanophenyl)propionate was 95/5). The reaction was performed according to the following equation:

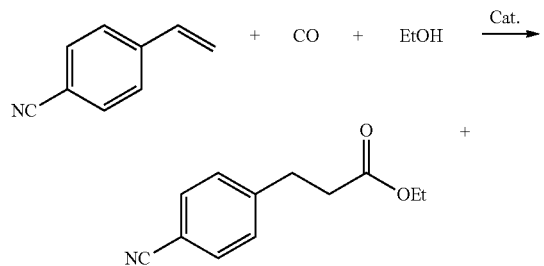

-continued

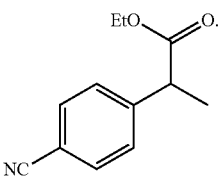

Various embodiments of the present disclosure may have one or more of the following effects. 1. The aryl bidentate phosphine ligand has both the rigid skeleton structure of the rigid ligand (triphenylphosphine structure) and the flexibility of the flexible ligand (the methylene group, which is easy to rotate). Such "flexibility with rigidity therein" may impart a suitable degree of flexibility to the ligand, which is conducive to the formation of the most favorable coordination mode in space and a relatively stable active structure. Therefore, it may show good catalytic activity and selectivity in the synthesis of organic carboxylic ester by olefin carbonylation. 2. Compared with the aliphatic phosphine ligands, which are widely used in the current hydroesterification, the aryl bidentate phosphine ligand used in the present disclosure may be advantageous in high stability as a simple synthesis method.

The above are only the preferred embodiments of the present disclosure. It should be pointed out that for those of ordinary skill in the art, without departing from the principle of the present disclosure, several improvements and modifications could be made, and these improvements and modifications shall fall within the scope of the present disclosure.

Many different arrangements of the various components depicted, as well as components not shown, are possible without departing from the spirit and scope of the disclosure. Embodiments of the disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A method for preparing an organic carboxylic ester, comprising the step of:

subjecting a terminal olefin, carbon monoxide, and an alcohol to a hydroesterification reaction in an organic solvent in the presence of a combined catalyst to generate an organic carboxylic ester having one more carbon atom than the terminal olefin, wherein the combined catalyst comprises a palladium compound, an aryl bidentate phosphine ligand, and an acidic additive; and the aryl bidentate phosphine ligand has a structural formula selected from the group consisting of the following formulas a, b, c, e, f, g, h, i, j, m, r, u, w, and x:

formula a, formula b, formula c, formula e, formula f, formula g, formula h, formula i, formula j, formula m, formula r, formula u, formula w, formula x 2. The method as claimed in claim 1, wherein:
a molar ratio of the aryl bidentate phosphine ligand to the palladium compound ranges from 0.1:1 to 100:1; and
a molar ratio of the acidic additive to the palladium compound ranges from 0.1:1 to 100:1.

3. The method as claimed in claim 2, wherein:
the molar ratio of the aryl bidentate phosphine ligand to the palladium compound ranges from 2:1 to 10:1; and the molar ratio of the acidic additive to the palladium compound ranges from 2:1 to 20:1.

4. The method as claimed in claim 1, wherein the palladium compound comprises at least one item selected from the group consisting of palladium acetate, palladium chloride, bis(triphenylphosphine)palladium dichloride, bis(acetonitrile)palladium dichloride, (1,5-cyclooctadiene)palladium dichloride, allylpalladium chloride, tetrakis(triphenylphosphine)palladium, palladium acetylacetonate, bis(dibenzylideneacetone)palladium, and tris(dibenzylideneacetone)dipalladium.

5. The method as claimed in claim 1, wherein the acidic additive comprises at least one item selected from the group consisting of perchloric acid, sulfuric acid, phosphoric acid, hydrochloric acid, formic acid, acetic acid, oxalic acid, methanesulfonic acid, trifluoromethanesulfonic acid, tert-butane-sulfonic acid, p-toluenesulfonic acid, 2-hydroxy-propane-2-sulfonic acid, 2,4,6-trimethylbenzenesulfonic acid, dodecyl sulfonic acid, and aluminum trifluoromethanesulfonate.

6. The method as claimed in claim 1, wherein the terminal olefin is an olefin having 2-20 carbon atoms.

7. The method as claimed in claim 6, wherein the olefin having 2-20 carbon atoms comprises at least one item selected from the group consisting of ethylene, propylene, 1-butene, cis-2-butene, trans-2-butene, isobutene, 1,3-butadiene, 1-pentene, cis-2-pentene, trans-2-pentene, 2-methyl-1-butene, 3-methyl-1-butene, 2-methyl-2-butene, hexene, tetramethylethylene, heptene, 1-octene, 2-octene, di-n-butene, diisobutene, n-decene, dodecene, hexadecene, and octadecene.

8. The method as claimed in claim 1, wherein:
an amount of the combined catalyst is based on an amount of the palladium compound relative to an amount of the terminal olefin; and
a molar amount of the palladium compound is 0.001-5% of a molar amount of the terminal olefin.

9. The method as claimed in claim 8, wherein the molar amount of the palladium compound is 0.05-1% of the molar amount of the terminal olefin.

10. The method as claimed in claim 1, wherein the alcohol is an aliphatic alcohol compound containing 1-20 carbon atoms.

11. The method as claimed in claim 1, wherein the alcohol comprises at least one item selected from the group consisting of methanol, ethanol, 1-propanol, isopropanol, isobutanol, tert-butanol, 1-butanol, 2-butanol, 1-pentanol, 2-pentanol, 3-pentanol, 1-hexanol, cyclohexanol, 2-ethylhexanol, isononanol, 2-propylheptanol, cyclohexane-1,2-diol, 1,2-ethylene glycol, 1,3-propylene glycol, glycerol, 1,2,4-butanetriol, 2-hydroxymethyl-1,3-propanediol, pentaerythritol, 1,2,6-trihydroxyhexane, and 1,1,1-tris(hydroxymethyl) ethane.

12. The method as claimed in claim 1, wherein the organic solvent comprises at least one item selected from the group consisting of alcohol, dioxane, tetrahydrofuran, 1,2-ethanediol dimethyl ether, tetraglyme, 1,2-diethoxyethyl ether, ethyl acetate, butyl acetate, benzene, toluene, anisole, xylene, dichloromethane, trichloromethane, and chloroform.

13. The method as claimed in claim 12, wherein, under the condition that the organic solvent is an alcohol, a molar ratio of the terminal olefin to the organic solvent ranges from 1:1 to 1:50.

14. The method as claimed in claim 1, wherein the hydroesterification reaction is performed at a pressure of 0.5-10.0 MPa and a temperature of 30-180° C.

15. The method as claimed in claim 14, wherein the hydroesterification reaction is performed at the pressure of 3-6 MPa and the temperature of 80-120° C.

16. The method as claimed in claim 2, wherein the hydroesterification reaction is performed at a pressure of 0.5-10.0 MPa and a temperature of 30-180° C.

* * * * *